(12) United States Patent
Bala et al.

(10) Patent No.: US 11,830,609 B1
(45) Date of Patent: *Nov. 28, 2023

(54) SYSTEM AND METHOD FOR DECEDENT MANAGEMENT TRACKING

(71) Applicant: Management Health Solutions, Inc., Tampa, FL (US)

(72) Inventors: Kishore Bala, Lutz, FL (US); Steven Herz, Tampa, FL (US); Justin Bays, Zionsville, IN (US)

(73) Assignee: MANAGEMENT HEALTH SOLUTIONS, INC., Tampa, FL (US)

( * ) Notice: Subject to any disclaimer, the term of this patent is extended or adjusted under 35 U.S.C. 154(b) by 135 days.

This patent is subject to a terminal disclaimer.

(21) Appl. No.: 17/303,582

(22) Filed: Jun. 2, 2021

Related U.S. Application Data (63) Continuation of application No. 17/247,138, filed on Dec. 1, 2020, now Pat. No. 11,049,610.

(51) Int. Cl.
  *G16H 40/20* (2018.01)
  *G16H 10/65* (2018.01)
  *G06K 19/06* (2006.01)

(52) U.S. Cl.
  CPC ....... *G16H 40/20* (2018.01); *G06K 19/06009* (2013.01); *G16H 10/65* (2018.01)

(58) Field of Classification Search
  CPC ... G16H 40/20; G16H 10/65; G06K 19/06009
  USPC ........................................................ 705/2–3
  See application file for complete search history.

(56) References Cited

U.S. PATENT DOCUMENTS

| | | | |
|---|---|---|---|
| 6,761,312 B2 | 7/2004 | Piatek et al. | |
| 6,948,271 B2 | 9/2005 | Helgeson et al. | |
| 9,449,441 B2* | 9/2016 | Hartmann | G07C 9/00 |
| 10,800,588 B2* | 10/2020 | Balwani | G06Q 10/0832 |
| 2014/0048593 A1* | 2/2014 | Hoganson | G16H 40/67 |
| | | | 206/459.5 |

(Continued)

OTHER PUBLICATIONS

Spoletini et al., Transplantation during the COVID-19 pandemic: nothing noble is accomplished without danger; Aug. 6, 2020; BMC Gastroenterology, 20:259; pp. 1-6; https://doi.org/10.1186/s12876-020-01401-0 (Year: 2020).*

(Continued)

*Primary Examiner* — Joy Chng
(74) *Attorney, Agent, or Firm* — SNELL & WILMER L.L.P.

(57) ABSTRACT

A system and method of tracking and managing a decedent to prevent a loss or misidentification of the decedent during transfer to a final disposition, such as a funeral home or crematorium. The system includes a server that may be integrated into an electronic health record, with the server automatically receiving data related to a decedent used to automatically create and populate a case file. The server associates a unique scannable indicium associated with the case file and the decedent, which is scanned throughout the process of transferring the decedent to a final disposition. Prior to the final transfer, the server notifies the final location of the pending transfer and includes a copy of the scannable indicium. Upon a verification of a match between the scannable indicium, the server authorizes a safe, secure, efficient, and consistent transfer of a decedent to a final location.

20 Claims, 1 Drawing Sheet

(56) References Cited

U.S. PATENT DOCUMENTS

2020/0342984 A1* 10/2020 Smith .................... G16H 15/00

OTHER PUBLICATIONS

Moncur et al., From death to final disposition: Roles of technology in the post-mortem interval, May 2012, Research Gate; pp. 1-11; https://www.researchgate.net/publication/239761292_From_death_to_final_disposition_Roles_of_technology_in_the_post-mortem_interval (Year: 2012).*

Spoletini et al., Transplantation during the COVID-19 pandemic; nothing noble is accomplished without danger; Aug. 6, 2020; BMC Gastroenterology, 20:259; pp. 1-6; httpss:/doi.org/10.1186/s12876-020-01401-0 (Year: 2020).

Moncur et al., From death to final disposition: Roles of technology in the post-mortem interval, May 2012, Research Gate; pp. 1-11; https://www.researchgate.net/publication/239761292_From_death_to_final_disposition_Roles_of_technology_in_the_post-morten_interval (Year: 2012).

Notice of Allowance dated Mar. 10, 2021 in U.S. Appl. No. 17/247,138.

* cited by examiner

SYSTEM AND METHOD FOR DECEDENT MANAGEMENT TRACKING

CROSS-REFERENCE TO RELATED APPLICATIONS

This nonprovisional application is a continuation of and claims priority to nonprovisional application Ser. No. 17/247,138, entitled "System and method for decedent management tracking," filed on Dec. 1, 2020, by the same inventors.

BACKGROUND OF THE INVENTION

1. Field of the Invention

This invention relates, generally, to decedent and appendage tracking systems. More specifically, it relates to a system and method of configuring workflows based on case types, including a system and method of creating and managing cases related to decedents and appendages, such that a component of the configurable system and method is designed to track a location and status of the decedents and appendages until a final disposition is reached.

2. Brief Description of the Prior Art

Upon the death of an individual or the loss of a limb or other body part, many different stakeholders must communicate with one another through a final disposition of the body or body part and associated required documentation. Depending on the circumstances surrounding the body or body part, these stakeholders include family members, physicians, medical examiners, emergency services, law enforcement personnel, healthcare administrators, infectious disease specialists, government entities, third-party transportation services, and funeral home operators. Decisions on a final disposition of the body or body part must be made quickly after a patient passes away, which is often a stressful time for stakeholders close to the patient. As such, it can be difficult to obtain timely decisions, and even more difficult to maintain a comprehensive tracking and documentation program through burial or cremation.

Typical decedent management systems rely on manual, paper-based forms. This is due, at least in part, to requirements that death certificates and other related forms be generated and maintained upon the death of an individual. However, such paper-based systems including non-linked forms fail to maintain an orderly management system, such that miscommunications and delays are common. Under the worst-case scenarios, such miscommunications can result in a loss of a body or body part. Particularly in the case of a decedent, the loss or misplacement of the decedent's body can pose not only immense emotional trauma for the decedent's loved ones, but also a public health and safety threat related to the disposal of a body.

Moreover, in light of the rise in infectious diseases, such as severe acute respiratory syndrome coronavirus 2 (SARS-CoV-2), robust decedent tracking and management systems are required to implement meaningful contact tracing systems in the hopes of slowing the spread of such infectious diseases. However, traditional manual, paper-based forms without managed workflows fail to provide such a robust tracking and management system, thereby failing to adequately trace the spread of infectious diseases, such as SARS-CoV-2.

While attempts have been made to automate portions of the decedent tracking and management system, no such attempt has proposed a fully automated system with integrated tracking from death to final disposition. For example, U.S. Pat. No. 6,761,312 to Piatek teaches a method of tracking victims of a mass casualty event. However, Piatek's system is limited to a tag including patient information that can be scanned to determine a patient's identity. A similar system is taught in U.S. Pat. No. 6,948,271 to Helgeson, which is directed to a removable band secured to a decedent usable for tracking a patient by scanning. U.S. Pat. No. 9,449,441 to Hartmann teaches an extension of such a system to provide multiple scanning tags so that a tissue sample can be scanned separately from a patient, if necessary. However, each of these systems fails to teach a comprehensive decedent tracking system, instead being limited to the simple scanning of a singular tag to receive information associated with that tag.

Beyond the simple identification scan, the prior art fails to provide a fully integrated and customizable tracking system that removes the need for paperwork to be manually associated with a patient, thereby providing an automated system that ensures a safe transfer of a decedent from death to final disposition. Accordingly, what is needed is a fully integrated system and method designed to track a location and status of the decedents and appendages until a final disposition is reached. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an efficient and consistent decedent tracking system and method is now met by a new, useful, and nonobvious invention.

The novel method of securely tracking a decedent and managing a disposition of the decedent includes a step of receiving, on a server, a set of data relating to a decedent. The set of data includes demographic information, a suspected cause of death, and additional information selected from the group consisting of blood type, exposure to a communicable disease, and decedent disposition preferences. For example, the set of data may include information relating to a diagnosis of severe acute respiratory syndrome coronavirus 2 related to the decedent. In such an embodiment, the method comprises a step of associating, via the server, an alert related to exposure to severe acute respiratory syndrome coronavirus 2 with the at least one scannable indicium associated with the case file, such that upon an occurrence of the scanning event associated with the at least one scannable indicium, the alert is configured to be transmitted to a stakeholder performing the scanning event.

The method includes a step of automatically creating, via the server, a case file associated with the decedent. The case file includes the set of data relating to the decedent, and includes a workflow including a set of tasks determined by the set of data relating to the decedent. After creating the case file, the method includes a step of automatically generating, via the server, a plurality of prepopulated forms depending on the set of data relating to the decedent and related to the set of tasks of the workflow.

The method includes a step of associating, via the server, an alert with at least one scannable indicium associated with the case file. The scannable indicium is associated with the set of data relating to the decedent. At least one scannable indicium is selected from the group consisting of a radio frequency identification, a real-time locating system, and a quick response code.

The method includes a step of tagging the decedent with a copy of at least one scannable indicium, such that a scanning event associated with the copy of at least one scannable indicium provides the set of data relating to the decedent, and such that the scanning event associated with the copy of at least one scannable indicium records a location of the decedent on the server. The step may include disposing a removable tag proximate to the decedent.

The server determines a final destination for a disposition of the decedent based on a preference predetermined by the decedent. The server then transmits a notification to the final destination, with the notification including a copy of at least one scannable indicium. The server verifies a match between the copy of at least one scannable indicium transmitted to the final destination, the copy of at least one scannable indicium associated with the decedent, and at least one scannable indicium associated with the case file. Based on a positive match verified by the server, the server terminates the case file and transferring custody of the decedent to the final destination.

In an embodiment, the method includes a step of transferring the decedent to an intermediary location selected from the group consisting of a medical examination location and an organ transplantation location. The server verifies a match between a copy of at least one scannable indicium transmitted to the intermediary location, the copy of at least one scannable indicium associated with the decedent, and at least one scannable indicium associated with the case file.

In an embodiment, the server is integrated into an electronic health record. In such an embodiment, the set of data related to the decedent is automatically transferred to the server via the electronic health record upon a death event associated with the decedent. If the decedent is transferred to an intermediary location configured to perform at least a portion of an organ transplantation, the method includes a step of automatically identifying, via the server integrated into the electronic health record, a match between the decedent and a transplant patient associated with the electronic health record.

In an embodiment, prior to the step of terminating, via the server, the case file, the method includes the step of prepopulating a final release form associated with the case file. The final release form includes a copy of at least one scannable indicium and a record of scanning events associated with at least one scannable indicium.

In an embodiment, the method includes a step of generating, on a server, a plurality of fields each configured to receive an input of an amount of information. The server organizes a plurality of case types based on the one or more sub-forms. Each of the plurality of case types includes a workflow including a set of tasks. The plurality of case types includes case types selected from the group consisting of an adult decedent, a child decedent, a neonatal decedent, and a decedent having an unknown cause of death. After associating the decedent with one of the plurality of case types and the associated workflow, the method includes a step of automatically generating, via the server, at least one of the one or more sub-forms associated with the associated one of the plurality of case types depending on the set of data relating to the decedent.

An object of the invention is to ensure an efficient and accurate transfer of a decedent post-expiration and pre-burial or cremation by associating an automatically generated and prepopulated case file with the decedent via a scannable indicium, thereby ensuring the identity of the decedent throughout the post-death transfer process.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a method and system of configuring a modular system to effectively manage case workflows, including a method and system of tracking and managing a decedent to prevent a loss or misidentification of the decedent during transfer to a final disposition, such as a funeral home or crematorium. The system includes a server that may be integrated into an electronic health record, with the server automatically receiving data related to a decedent used to automatically create and populate a case file. The server associates a unique scannable indicium with the case file and the decedent, which is scanned throughout the process of transferring the decedent to a final disposition. The unique scannable indicium can be initially generated by a hospital, clinic, electronic health record, or other medical record system associated with a patient prior to entry into the system of the present invention; alternatively, the system can generate the unique scannable indicium to be associated with the decedent. Prior to the any transfer of the decedent, such as a final transfer of the decedent to a stakeholder such as a funeral home or crematorium, or such as an intermediary transfer of the decedent to a coroner or medical examiner, the server notifies the recipient location of the pending transfer and includes a copy of the scannable indicium. Upon a verification of a match between the scannable indicium, the server authorizes a safe, secure, efficient, and consistent transfer of a decedent to a subsequent location.

As noted above, the system is configurable depending on the case management requirements of a particular facility which can depend on local, state, or federal requirements depending on a death type. Moreover, requirements can vary depending on policy changes; as such, a modular and configurable system allows system administrators to customize each aspect of the system to ensure compliance with requirement and an optimal workflow for each case. To that end, the system provides for the configuration of workflows that include fillable fields that receive data from a user input, an electronic health record, a scannable form, or other data capture methods known within the art. As such, upon configuration, an administrator preselects one or more fields of data to be used within a component of a case management file, depending on the type of case. The fields of data used within the system are infinitely customizable, including inputs such as a decedent's name, date of birth, a pronouncing physician, the date of death, a transportation date, a final disposition location, a cause of death, and any other data point usable in case management within the system (such as for decedent management and tracking). In addition, the system provides options for a type of data input for each field, such as a fill-in box (which can also automatically receive data from an internal or external source, such as the electronic health record), a drop-down menu with predetermined selections, or other data input mechanisms.

After the plurality of required fields are received within the system, the system provides the capability to generate one or more sub-forms within the management system. The sub-forms utilize one or more of the fields to direct a data capture protocol of each sub-form, such that required data for a particular sub-form are captured for a particular sub-form. For example, a sub-form be labeled as "Decedent Information" and can include identifying information about a particular decedent within a case file. On the sub-form for "Decedent Information," fields such as the decedent's name, the decedent's date of birth, the pronouncing physician, the decedent's date of death, and next-of-kin details for the decedent, may appear as fields required for the completion of the "Decedent Information" sub-form. The goal of each sub-form is the accumulation of data from related fields under an organized category to improve efficiencies related to the generation of various required forms within the workflow of a case file.

The sub-forms and accumulated, organized data from the fields are then further organizable into documents, which can be finalized documents required for case transfer, other case completion requirements within the workflow, or other important documents required during the workflow of a case. The documents include one or more sub-forms, such that the data stored in the various fields discussed above are organized into a finalized document that can be used within the workflow. For example, during decedent management and tracking, it is often desired or required to generate a memorandum of death that is reportable or usable by a government or regulatory agency, such as a state or federal death reporting database. The memorandum of death must include a certain amount of information, which may vary depending on facility, local, state, and/or federal requirements. As such, the required information as captured via fields of data input captured during the processes described above, and as organized via sub-forms that serve to organize accumulated data from the fields, can be prepopulated into a finalized document that is usable within the workflow of the decedent's case management.

Moreover, in an embodiment, the system is integrated into a government or regulatory database, such as a state death registry, such that a finalized set of data can be automatically transferred to the state death registry to initiate and complete creation and finalization of a death certificate, as opposed to relying on a manually-generated form that is prone to human error. The customization, including real-time editing of fields, sub-forms, and documents via addition and/or deletion of one or more of the same, provides flexibility within the system to comply with required protocols and regulations, while improving data transfer and recordation accuracy and ultimate workflow efficiency. Moreover, the configurability of the system provides for integration into death registries of various government and regulatory databases, which typically require different field, sub-forms, and documents to be input into the database; rather than relying on a manual input, the system determines which regulatory agency is required for a particular case, manages a workflow for the agency accordingly, and integrates the data into the agency upon completion of the case, as will be discussed in more detail below.

The fields, sub-forms, and documents are organized into one or more workflows that depend on a final document that is required for a completion of a particular type of case, such that different types of cases include different workflows. For example, a situation in which the system is implemented for decedent management and tracking, a different workflow would be required for an expected death of an adult individual arriving from a hospice setting, as opposed to an unexpected death of an adult individual for which a cause of death is unknown, and as opposed to a death of a neonatal individual. As such, workflows requiring different fields of data, as populated by different sub-forms and organized into different forms, would be required, resulting in the system including a plurality of different workflows designed to encompass every type of decedent that could be entered into the system. These workflows determine an order of tasks to be performed and completed from the arrival of a decedent through a final disposition of the decedent, with each task including a target time to completion and an urgent deadline to completion as predetermined and configured based on the particular task. The workflows and the system will be discussed in greater detail below.

Accordingly, upon setup of the system, various protocols, or workflows, are preset depending on data categories or fields such as the type of death (such as a child decedent, a neonatal decedent, an adult decedent, circumstances surrounding the death, and the status of the decedent's appendages), patient post-death plans, and local, federal, and facility-based requirements. As such, in the event of a casualty within a facility or prior to arrival at a facility, the system prepopulates a set of forms, guides, and checklists to ensure a safe and consistent disposition of the decedent. Moreover, as an example, if a jurisdiction requires a medical autopsy be performed for cases in which a cause of death is unknown, the system receives a request to include an examination by a medical examiner within the workflow for the decedent. The system then generates a set of instructions related to the transfer of the decedent to medical examiner (as will be described in detail below), the receipt of results from the examination performed by the medical examiner, and the consistent and efficient transfer of the decedent from the medical examiner to the next stakeholder within the chain of custody. Accordingly, by prepopulating an amount of forms depending on the required or desired chain of custody, the system manages the disposition of the decedent from arrival until final disposition based on the fields, sub-forms, and document described in detail above. Moreover, depending on the jurisdiction, facility, or patient, the prepopulated forms, guides, and checklists are customizable upon setup of the system, such that certain death events and post-death plans trigger different sets of instructions derived from the back-end data capture and organization provided by the system. As such, a facility can automate the entirety of the post-death process based on infinitely configurable protocols, such as a simple input of a death type and patient wishes, such that every required form is automatically generated and prepopulated when data is available or captured, thereby improving accuracy, compliance and decreasing a risk of misplacing a decedent.

Figure 1:
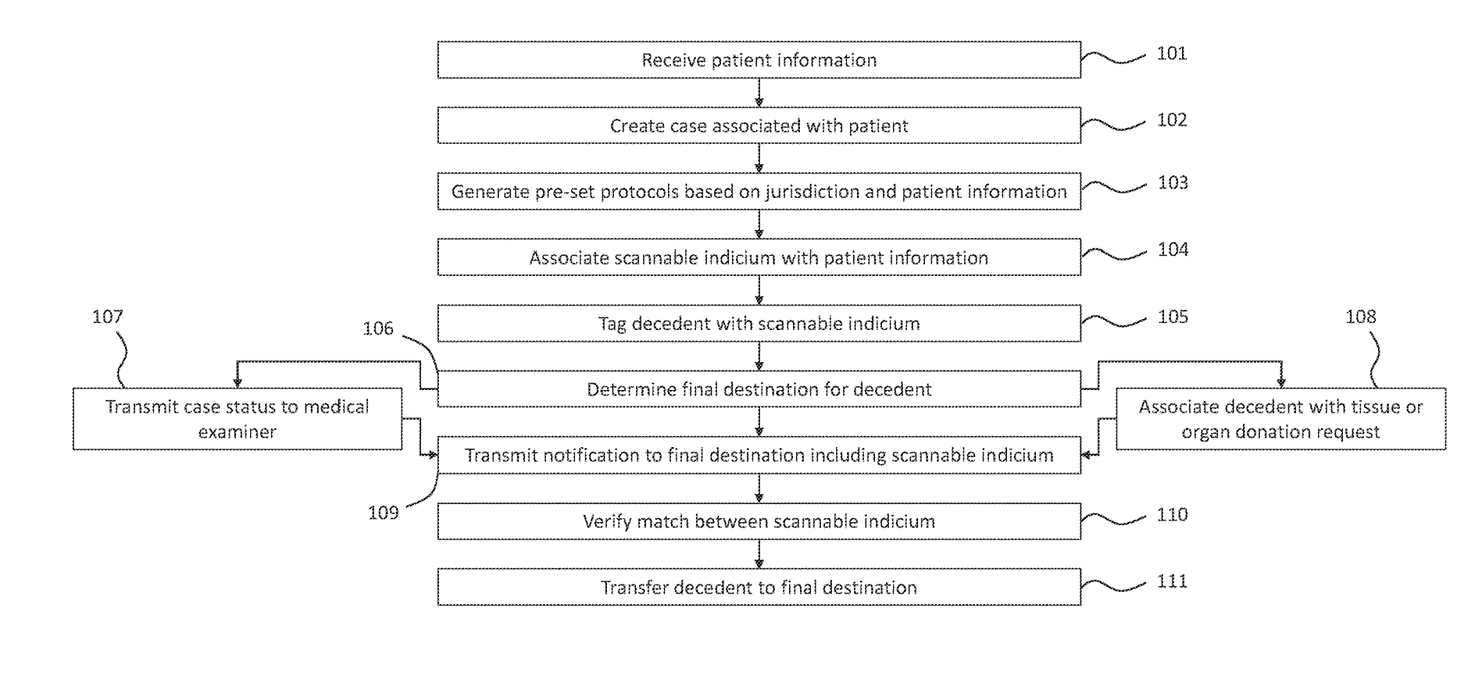
The FIGURE is a process flow diagram depicting an embodiment of a decedent management system, including a method of associating patient information with a tracking device to match a patient with transportation information, thereby ensuring that the patient arrives at a final destination.

Referring now to The FIGURE, a method of decedent tracking in accordance with an embodiment of the present invention is depicted in a process-flow diagram. The method begins at step 101, which includes the system receiving information relating to a patient who has recently died (i.e., the decedent). The information can include patient identification information, important medical information (such as blood type and the suspected cause of death), risks associated with the patient (including exposure to a communicable disease, such as SARS-CoV-2, or exposure to radiation or another harmful substance), patient disposition wishes, and other post-death information that determines the chain of custody for the decedent. In an embodiment, the system is integrated into an electronic health record (EHR), and the information is automatically received within the decedent management tracking portion of the system from the integrated EHR. In addition, the information can automatically populate upon arrival via an electronic message or notification of death, including the patient information discussed above.

However, under certain situation, the EHR may not update in a timely fashion and may not transmit a notification to the system of a death event for several hours or days after an event takes place, long after a desired time to transfer the decedent to a subsequent location within the chain of custody as determined by the workflow. As such, the system is in constant electronic communication with the EHR and the databases of the various stakeholders utilizing the system, such that the system receives automated updates of patient information in real-time on a back-end of the system. As such, the system receives and/or automatically captures and populates information required to be included in one or more fields usable to determine the workflow of a decedent's case within the system in a background process, thereby freeing the electronic devices associated with the system to perform other tasks in real time without the need for the heavy processing involved with data input and transfer. Moreover, by receiving the information required for the population of fields, sub-forms, and documents, the system maintains a real-time workflow management protocol without relying on information being pushed to the system from an EHR, thereby drastically reducing the likelihood of a miscommunication or incorrect transfer of a decedent. Moreover, the information can be manually input into the decedent management system.

During step 102, after or simultaneous with receiving the patient information in step 101, the system creates a case that is associated with the patient, either automatically or by receiving a request to create a case within a certain workflow, in accordance with the discussion in the sections above. In particular, as noted in the sections above, the creation of the case by the system and the determination of a workflow for the decedent is dependent on factors such as the suspected or likely cause of death, patient disposition wishes, local, federal, and facility-based requirements, and other factors required in the determination of intermediary and final dispositions of the decedent during the case management process. As such, the type of case and the workflow created by the system depends on the information received during step 101.

After the case is created, as noted above, the system generates pre-set protocols, forms, guides, and checklists depending on the type of case created for the patient during step 103. These forms are prepopulated by the system depending on the information received during step 101 and the type of case selected during step 102. As such, the system automates the process of not only receiving relevant information related to a decedent, but also of generating the required digital paperwork to accompany the decedent, thereby ensure that the required forms are directly associated with the decedent. As noted above, since the system automatically performs these tasks as background processes, the system is free to perform additional manual tasks on a front-end component, thereby improving the speed at which data is captured and associated with a decedent's file.

Next, during step 104, at least one scannable indicium is associated with the patient information received during step 101, the type of case selected during step 102, and the pre-set protocols generated during step 103. Typically, a facility from which the decedent arrives utilizes a unique code that is associated with an individual patient, such that medications administered to and services provided for the patient can be easily associated with the patient within the facility's electronic health record. Upon a death event associated with the patient, the unique code remains associated with the patient, often both electronically and physically in the form of a tag physically attached to the patient. As such, the system can utilize the unique code, or scannable indicium, already associated with the patient to associate the scannable indicium with the decedent during workflow management of the decedent post-death. Alternatively, the system can automatically generate and associate a scannable indicium with the decedent, thereby associating the decedent with the patient information and case within the workflow. Regardless of the origin of the scannable indicium, the system thereby binds the decedent to the scannable indicium within the system and the workflow for the decedent for safe, secure, and efficient decedent management and tracking throughout the transportation process. In an embodiment, the scannable indicium is a radio frequency or other real-time locating system; in other embodiments, the scannable indicium is a quick response or other similar code. Moreover, during step 105, the decedent is tagged with a copy of at least one scannable indicium, such as via a temporary and removable tag. During each subsequent step, each stakeholder involved in the chain of custody of the decedent utilizes the system to not only ensure the identity and requirements of the decedent, but also review and input information related to the various tasks in the workflow generated for the decedent. As such, each stakeholder can view updated information related to the decedent in real time.

Next, during step 106, a final destination is determined by the system based on a number of factors, including the decedent's post-death plan, facility protocols, the chain of custody of the decedent (i.e., if the decedent must undergo an autopsy, medical examination, or other mandated steps post-death and pre-burial or cremation), and other factors relevant in determining the optimal final destination of the decedent. In addition, in an embodiment, the proximity of local funeral homes and/or cremation facilities is a factor in determining a final disposition location based on a calculation of distances, such as in the absence of a decedent's post-death plan. Accordingly, the system thereby receives a request to associate the decedent with his or her final destination, such that the remaining steps of the method are directed to achieving the safe and timely transfer of the decedent to a final resting location.

During the workflow generated for a particular decedent, it may be desirable to transport the decedent to an intermediary location for additional testing prior to a final disposition, such as a burial or a cremation. For example, if the cause of death remains unknown, it may be advantageous to perform an autopsy or other medical examination of the decedent to determine a cause of death. This is particularly true if there are suspicious or uncertain circumstances surrounding the cause of death, such as during a homicide or accident, and the cause of death must be determined and recorded based on regulatory or government requirements. In addition, this may be true if the decedent may have been exposed to a communicable disease or virus, and an ongoing risk to public safety exists related to the decedent. For example, during the SARS-CoV-2 pandemic, it is hypothesized that the number of deaths in various communities above average is greater than the recorded number of deaths attributed to SARS-CoV-2. As such, it is likely that undetected examples of SARS-CoV-2-related deaths have occurred during the community spread of the airborne virus; the only way to determine the amount of such deaths in the absence of a positive test results prior to death is to perform an autopsy or other medical examination.

Accordingly, during step 107, the case status associated with the decedent is transferred from the system to a medical examiner. Similar to the previous steps, the system automatically performs this step as a result of the workflow generated for the decedent; as such, the necessary protocols involved in the transfer are automatically prepopulated by the system if a medical examination of the decedent is required upon the generation of the patient case during step 102. Typically, such a case status transfer and chain of custody transfer occurs via manual paperwork matching; however, such typical cases can result in mismatched identification information and actual decedents, leading to autopsies performed on incorrect decedents. However, the system automates the case status transmission step to not only prevent such mismatching information and mistaken autopsies from happening, but also to free up the front-end of the system (and its users) to perform other tasks simultaneous to the information transfer. Accordingly, the decedent can be temporarily transferred to a medical examiner to perform additional testing, such as to determine a cause of death or the presence of a communicable disease to assess risks associated with those who interacted with the decedent prior to expiration (i.e., to perform contact tracing on the decedent). The steps involved in the safe transfer of the decedent between locations will be discussed below.

In addition, certain decedents may opt to donate tissue samples or organs for use in patients needing organ transplants or tissue-based therapies. Accordingly, during step 108, the decedent can be transferred to an in-house or external location for organ, limb, tissue, or other body part removal for the purpose of an implant into a live patient or other use, such as a scientific examination for research purposes. Similar to the previous steps, the system automatically performs this step as a result of the workflow generated for the decedent. Moreover, the necessary protocols involved in the transfer are automatically prepopulated by the system if the system receives a notification or receives a data input via a fillable field, as described above, that the decedent's organs, tissues, or other appendages should be removed for implantation upon the generation of the patient case during step 102.

The removed one or more body parts can be associated via the system with a secondary scannable indicium according to the steps outlined above, such that the relevant patient information is associated with the body parts as well. For example, to ensure a quick, efficient, and accurate organ transplant match, the decedent's blood type and other relevant identification information can be associated with the removed body parts such that the system can automatically identify a transplant candidate. In an embodiment in which the system is integrated into an EHR, the system can communicate an availability of a certain organ to the EHR for the purpose of identifying a match to another patient within the EHR, thereby ensuring the timely transplantation of the organ to the patient in need. Similar to the transfer of the decedent to the medical examiner during step 107 described above, the steps involved in the safe transfer of the decedent to and from the autopsy location will be discussed below.

Next, during step 109, the system transmits a notification to a final destination that the decedent will be transferred to that particular location. Step 109 can be performed directly after step 106, during which the final destination for the decedent is determined by the system, or after one or more of steps 107 (transmitting the decedent and the decedent's case status to a medical examiner for further testing and analysis) and 108 (transmitting the decedent and the decedent's case status to an organ removal location for transplantation) are completed, if necessary.

During step 109, the system pre-generates a final release form that is associated with the decedent. The final release form includes prepopulated information derived from the previous steps of the method, including the decedent's information and risk factors, the contact information for the final destination, the scannable indicium associated with the decedent, and any results from examinations performed on the decedent during previous steps. Moreover, during step 109, the system transmits a request via wired or wireless communications to the final destination to transfer custody of the decedent via a physical transfer. The notification includes a copy of the scannable indicium as a prepopulated transfer of information; as such, a stakeholder representing the final destination, a stakeholder from the system side, and the decedent himself or herself, each include a copy of the scannable indicium. Accordingly, during step 110, the system verifies a match between the decedent's copy of the scannable indicium (which matches that of the system) and the final destination's copy of the scannable indicium.

Since the system is designed for accuracy within the chain of custody for the decedent, the likely scenario is that the scannable indicia match between all interested parties. As such, the method proceeds to step 111, during which the system transfers custody of the decedent to the final destination. During step 111, the system completes the decedent's case status by automatically generating a memorandum of death certificate including a summary of the case status and the previous steps taken with respect to the decedent. The system saves a copy of the case status and memorandum of death certificate in the event that the case must be reopened at a later date. However, in the unlikely event of a non-match between the indicia, the system rejects the request to transfer custody from the system to the final destination. As such, the system ensures a safe, secure, and efficient transfer of the decedent to the final destination in accordance with federal, local, and facility-based requirements, as well as the decedent's post-death plan.

Accordingly, by utilizing the system, the various stakeholders related to a decedent and the decedent's safe transfer to a final destination ensure that mistaken identities or other misdirection events related to the decedent do not occur during the various tasks that must be accomplished post-death. Rather than relying on traditional paperwork and other manual tasks performed by medical professionals and funeral home personnel, the system automates the generation, population, and data transfers related to decedent information and the tasks involved in transferring custody to a final destination. Moreover, the system performs these steps in background tasks in automated and real-time data receipt and transfer, thereby allowing system users to interact with different portions of the system without significantly reducing system memory for those additional tasks performed via the system. In addition, while the description above focuses primarily on decedent management and tracking, it should be noted that the systems and methods described above can be implemented in various workflow management and tracking systems. For example, the system's configurability of fields, sub-forms, and documents, together with the system's tracking and accountability components, can be used in the tracking and management of inventory items, such as vaccines that are difficult to transport and require real-time tracking and management. Such vaccine storage and distribution workflows can be configured as a module of the system using the fields, sub-forms, and documents described in detail in the sections above.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C #, C++, Visual Basic or the like and conventional procedural programming languages, such as the "C" programming language or similar programming languages.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method comprising:
   receiving, on a server, a set of data relating to a decedent, the set of data including at least demographic information and a decedent disposition preference;
   automatically creating, via the server, a case file associated with the decedent, the case file including the set of data relating to the decedent, the case file including a workflow including a set of tasks determined by the set of data relating to the decedent;
   automatically generating, via the server and in response to creating the case file, at least one prepopulated form depending on the set of data relating to the decedent and relating to the set of tasks of the workflow;
   associating, via the server, at least one scannable indicium with the case file, the at least one scannable indicium associated with the set of data relating to the decedent;
   tagging the decedent with a copy of the at least one scannable indicium, such that a scanning event associated with the copy of the at least one scannable indicium provides the set of data relating to the decedent;
   for each scanning event associated with the copy of the at least one scannable indicium, recording a location of the decedent and transmitting the recorded location to the server to create a record of scanning events associated with the copy of the at least one scannable indicium;
   determining, via the server, a final destination for a disposition of the decedent based on the decedent disposition preference;
   transmitting, via the server, a notification to the final destination, the notification including a copy of the at least one scannable indicium;
   verifying, via the server, a match between the copy of the at least one scannable indicium transmitted to the final destination and the copy of the at least one scannable indicium associated with the decedent; and
   based on the verifying the match by the server, completing, via the server, the case file and transferring custody of the decedent to the final destination.

2. The method of claim 1, further comprising:
   transmitting, via the server, a notification to an intermediary location, the notification including a copy of the at least one scannable indicium, the intermediate location selected from the group consisting of a medical examination location and an organ transplantation location;
   transferring the decedent to the intermediary location;
   scanning the copy of the at least one scannable indicium transmitted to the intermediary location to record a location of the decedent; and
   transmitting the recorded location to the server.

3. The method of claim 2, further comprising the steps of:
   verifying, via the server, a match between the copy of the at least one scannable indicium transmitted to the intermediary location and the copy of the at least one scannable indicium associated with the decedent; and
   based on the verifying the match by the server, transferring custody of the decedent to the intermediary location.

4. The method of claim 1, wherein the set of data includes exposure to a communicable disease, wherein the communicable disease is severe acute respiratory syndrome coronavirus 2.

5. The method of claim 4, further comprising associating, via the server, an alert related to exposure to severe acute respiratory syndrome coronavirus 2 with the at least one scannable indicium associated with the case file, such that upon an occurrence of the scanning event associated with the at least one scannable indicium, the alert is configured to be transmitted to a stakeholder performing the scanning event.

6. The method of claim 1, wherein the server is integrated into an electronic health record.

7. The method of claim 6, wherein the receiving, on the server, the set of data relating to the decedent further comprises automatically receiving, in real-time, the set of data related to the decedent at the server from the electronic health record.

8. The method of claim 6, further comprising transferring the decedent to an intermediary location configured to perform at least a portion of an organ transplantation.

9. The method of claim 8, further comprising automatically identifying, via the server integrated into the electronic health record, a match between the decedent and a transplant patient associated with the electronic health record.

10. The method of claim 1, wherein the at least one scannable indicium is selected from the group consisting of a radio frequency identification, a real-time locating system, and a quick response code.

11. The method of claim 1, wherein the tagging the decedent with the copy of the at least one scannable indicium includes disposing a removable tag including the copy of the at least one scannable indicium proximate to the decedent.

12. The method of claim 1, wherein prior to the completing, via the server, the case file, prepopulating a final release form associated with the case file, the final release form including the set of data relating to the decedent, a copy of the at least one scannable indicium, and the record of scanning events associated with the copy of the at least one scannable indicium.

13. A method of comprising:
    generating, on a server, a plurality of fields each configured to receive an input of information;
    organizing, via the server, the plurality of fields into one or more sub-forms, such that each of the one or more sub-forms includes an amount of information organized into a category;

generating, via the server, a plurality of case types based on the one or more sub-forms, each of the plurality of case types including a workflow including a set of associated tasks, the plurality of case types including case types selected from the group consisting of an adult decedent, a child decedent, a neonatal decedent, and a decedent having an unknown cause of death;

receiving, on the server, a set of data relating to a decedent, the set of data including demographic information and a decedent disposition preference;

associating, via the server, the decedent with one of the plurality of case types and an associated workflow as determined by the set of data relating to the decedent;

in response to associating the decedent with one of the plurality of case types and the associated workflow, automatically generating, via the server, at least one of the one or more sub-forms associated with the associated one of the plurality of case types depending on the set of data relating to the decedent;

associating, via the server, at least one scannable indicium with the workflow, such that the at least one scannable indicium associated with the set of data relating to the decedent;

tagging the decedent with a copy of the at least one scannable indicium, such that a scanning event associated with the copy of the at least one scannable indicium provides the set of data relating to the decedent;

for each scanning event associated with the copy of the at least one scannable indicium, recording a location of the decedent and transmitting the recorded location to the server for recordation within the workflow to create a record of scanning events associated with the copy of the at least one scannable indicium;

determining, via the server, a final destination for a disposition of the decedent based on the decedent disposition preference;

transmitting, via the server, a notification to the final destination, the notification including a copy of the at least one scannable indicium;

verifying, via the server, a match between the copy of the at least one scannable indicium transmitted to the final destination and the copy of the at least one scannable indicium associated with the decedent; and based on a positive match verified by the server, completing, via the server, the workflow of the associated one of the plurality of case types and transferring custody of the decedent to the final destination.

14. The method of claim 13, wherein the set of data includes exposure to a communicable disease, wherein the communicable disease is severe acute respiratory syndrome coronavirus 2.

15. The method of claim 14, further comprising associating, via the server, an alert related to exposure to severe acute respiratory syndrome coronavirus 2 with the at least one scannable indicium associated with the workflow, such that in response to an occurrence of the scanning event associated with the at least one scannable indicium, the alert is configured to be transmitted to a stakeholder performing the scanning event.

16. The method of claim 13, further comprising transferring the decedent to an intermediary location configured to perform at least a portion of an organ transplantation.

17. The method of claim 13, wherein the server is integrated into an electronic health record.

18. The method of claim 17, wherein the receiving, on the server, the set of data relating to a decedent further comprises automatically receiving, in real-time, the set of data related to the decedent at the server from an electronic health record.

19. The method of claim 13, wherein the at least one scannable indicium is selected from the group consisting of a radio frequency identification, a real-time locating system, and a quick response code.

20. The method of claim 13, wherein prior to the completing, via the server, the workflow of the associated one of the plurality of case types, prepopulating a final release form associated with the workflow and based on the set of tasks, the final release form including the set of data relating to the decedent, a copy of the at least one scannable indicium, and the record of scanning events associated with the copy of the at least one scannable indicium.

* * * * *